United States Patent
Kravtchenko et al.

(10) Patent No.: US 7,217,299 B2
(45) Date of Patent: May 15, 2007

(54) DYE COMPOSITION COMPRISING AT LEAST ONE DIRECT DYE OF THE AZO-PYRIDINIO-PYRIDONE FAMILY AND AT LEAST ONE DIFFERENT SYNTHETIC DYE, AND PROCESS

(75) Inventors: Sylvain Kravtchenko, Asnieres (FR); Alain Lagrange, Coupvray (FR); Frédéric Guerin, Paris (FR)

(73) Assignee: L'Oreal S.A., Paris (FR)

( * ) Notice: Subject to any disclaimer, the term of this patent is extended or adjusted under 35 U.S.C. 154(b) by 308 days.

(21) Appl. No.: 11/030,053

(22) Filed: Jan. 7, 2005

(65) Prior Publication Data

US 2005/0172422 A1   Aug. 11, 2005

Related U.S. Application Data

(60) Provisional application No. 60/549,538, filed on Mar. 4, 2004.

(30) Foreign Application Priority Data

Jan. 7, 2004 (FR) .................................. 04 50040

(51) Int. Cl.
*A61K 7/13* (2006.01)
(52) U.S. Cl. ................ 8/405; 8/406; 8/408; 8/410; 8/411; 8/412; 8/425; 8/451; 8/568; 546/255
(58) Field of Classification Search ............ 8/405, 8/406, 408, 410, 411, 412, 425, 451, 568; 546/255
See application file for complete search history.

(56) References Cited

U.S. PATENT DOCUMENTS

| | | | |
|---|---|---|---|
| 4,003,699 A | | 1/1977 | Rose et al. |
| 4,087,244 A | | 5/1978 | Greve et al. |
| RE30,199 E | | 1/1980 | Rose et al. |
| 5,015,292 A | * | 5/1991 | Bruder et al. ............ 106/31.48 |
| 5,061,289 A | | 10/1991 | Clausen et al. |
| 5,380,340 A | | 1/1995 | Neunhoeffer et al. |
| 5,536,267 A | | 7/1996 | Edwards et al. |
| 5,663,366 A | | 9/1997 | Neunhoeffer et al. |
| 5,708,151 A | | 1/1998 | Möckli |
| 5,766,576 A | | 6/1998 | Löwe et al. |
| 5,888,252 A | | 3/1999 | Möckli |
| 6,099,592 A | | 8/2000 | Vidal et al. |
| 6,284,003 B1 | | 9/2001 | Rose et al. |
| 6,338,741 B1 | | 1/2002 | Vidal et al. |
| 6,645,258 B2 | | 11/2003 | Vidal et al. |
| 2002/0050013 A1 | | 5/2002 | Vidal et al. |
| 2003/0019051 A9 | | 1/2003 | Vidal et al. |

FOREIGN PATENT DOCUMENTS

| | | |
|---|---|---|
| CH | 601 432 | 7/1978 |
| DE | 23 59 399 | 6/1975 |
| DE | 38 43 892 | 6/1990 |
| DE | 41 33 957 | 4/1993 |
| DE | 195 43 988 | 5/1997 |
| EP | 0 714 954 | 6/1996 |
| EP | 1 133 975 A1 | 9/2001 |
| FR | 2 733 749 | 11/1996 |
| GB | 1 026 978 | 4/1966 |
| GB | 1 153 196 | 5/1969 |
| GB | 2 173 210 A | 10/1986 |
| JP | 2-019576 | 7/1988 |
| JP | 5-163124 | 12/1991 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 03/029359 | 4/2003 |

OTHER PUBLICATIONS

STIC Search Report dated Nov. 27, 2006.*
"Dyes and Dye Intermediates" *Kirk-Othmer Encyclopaedia of Chemical Technology*, 4th ed., vol. 8; Wiley & Sons, 1993.
English language Derwent Abstract of JP 2-019576.
English language Derwent Abstract of JP 5-163124.
French Search Report for French Patent Application No. FR 04/50040 (prioirty document for present application).

* cited by examiner

*Primary Examiner*—Eisa Elhilo
(74) *Attorney, Agent, or Firm*—Finnegan Henderson Farabow Garrett & Dunner, LLP

(57) ABSTRACT

The present invention relates to a dye composition comprising, as direct dye, at least one dye of the azo-pyridinio-pyridone family and at least one synthetic dye different from the first dye.

The invention also relates to a process for dyeing keratin fibers, e.g., human keratin fibers such as the hair, and to a multi-compartment device for implementing it.

20 Claims, No Drawings

DYE COMPOSITION COMPRISING AT LEAST ONE DIRECT DYE OF THE AZO-PYRIDINIO-PYRIDONE FAMILY AND AT LEAST ONE DIFFERENT SYNTHETIC DYE, AND PROCESS

This application claims benefit of U.S. Provisional Application No. 60/549,538, filed Mar. 4, 2004.

The present disclosure relates to a dye composition comprising, as direct dye, at least one dye of the azo-pyridinio-pyridone family, and at least one synthetic dye different from the azo-pyridinio-pyridone dye, and also to a process for dyeing keratin fibers, especially human keratin fibers such as the hair, using the composition.

There are essentially two types of dyeing used for keratin fibers: "permanent" dyeing and "semi-permanent" dyeing.

The first, also known as oxidation dyeing, uses "oxidation" dye precursors, which are colorless or weakly colored compounds. Once mixed with oxidizing products at the time of use, these precursors lead to colored and coloring compounds via a process of oxidative condensation. Very fast and strong colors are thus obtained.

As oxidation dye precursors, compounds known as oxidation bases are generally used, for instance para-phenylenediamines and para-aminophenols. The oxidation bases may be combined, where appropriate, with at least one other compound, known as a coupler, with the aim of varying the shades of the colors obtained.

Although it is possible, by virtue of the large number of possible base/coupler combinations, to obtain a wide range of colors, problems of variation in the fastness or selectivity may occasionally arise from one compound to another, which are difficult to control, resulting in a change of the color.

Finally, oxidation dyeing is not always entirely satisfactory when it is desired to obtain dark shades, and more particularly greys and blacks.

The second dyeing route, known as direct dyeing, represents an advantageous (in certain respects) alternative to oxidation dyeing. This is because, unlike oxidation dyeing, it does not require the use of an oxidizing agent in alkaline medium, which contributes towards making this dyeing method less aggressive than the first method with respect to the fiber treated, and thus can cause less degradation of the fiber.

Direct dyeing specifically comprises coloring the hair by causing a colored molecule, which remains of relatively small size, to penetrate into the hair by diffusion. These compounds make it possible to obtain chromatic color uptakes.

However, one of the drawbacks of direct dyeing is that it may be considered too selective. Furthermore, the coloration is sparingly fast, i.e., may not hold up well, especially with respect to shampoo.

Thus, it would be desirable to solve at least one of the problems mentioned above. Accordingly, the present inventors propose a dye composition comprising direct dyes, for obtaining satisfactory color uptake on keratin fibers, irrespective of their degree of sensitization, and for allowing access to natural, very strong, sparingly selective colorations in varied dark shades, which may show a very good level of fastness and which may not change color over time. For example, very high-quality grey and black shades may be obtained.

The present disclosure, therefore, relates to a dye composition comprising, in a medium that is suitable for dyeing keratin fibers, such as human keratin fibers, a) at least one dye of formula (I) below:

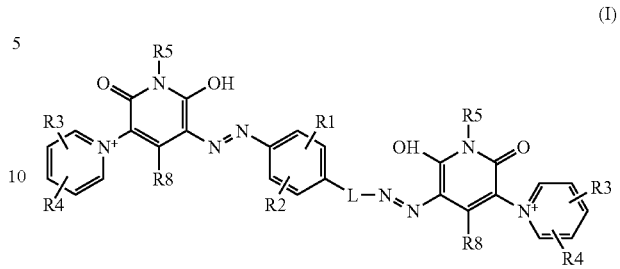

(I)

in which:

$R_1$ and $R_2$, independently of each other, are chosen from:
  a hydrogen atom;
  linear and branched $C_1$–$C_4$ alkyl groups, optionally substituted with at least one group chosen from hydroxyl, amino, halogen, such as chlorine, bromine and fluorine, and $C_1$–$C_3$ alkyl groups;
  linear and branched $C_1$–$C_4$ alkoxy groups;
  a group chosen from hydroxyl, amino, halogen and linear and branched $C_1$–$C_3$ alkoxy groups;

$R_3$ and $R_4$, independently of each other, are chosen from:
  a hydrogen atom;
  linear and branched $C_1$–$C_4$ alkyl groups, such as a methyl group;
  carboxylic groups, in acid or salified form, and linear and branched $C_1$–$C_6$ carboxyalkyl groups;
  linear and branched $C_1$–$C_6$ alkoxy groups;

$R_5$ is chosen from:
  a hydrogen atom;
  linear and branched $C_1$–$C_4$ alkyl groups;
  linear and branched $C_1$–$C_6$ alkenyl groups, substituted with a group $(R_6R_7N-)_n$, wherein n is equal to 0 or 1 and, when n=1, $R_6$ and $R_7$ are chosen from, independently of each other, a hydrogen atom and linear and branched $C_1$–$C_6$ alkyl groups, optionally substituted with at least one group chosen from hydroxyl, amino, halogen, such as chlorine, bromine and fluorine, and $C_1$–$C_3$ alkyl groups;

$R_8$ is chosen from:
  a hydrogen atom;
  linear and branched $C_1$–$C_6$ alkyl groups, such as methyl and ethyl groups;

L is a divalent group of formula L1 or L2 below:

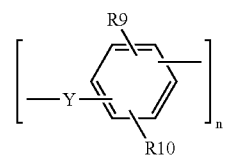

L1

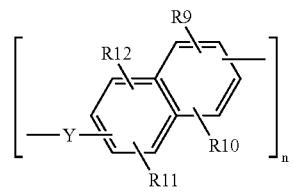

L2 in which:
n is equal to 0 or 1;
$R_9$, $R_{10}$, $R_{11}$ and $R_{12}$ are chosen from, independently of each other:
a hydrogen atom;
linear and branched $C_1$–$C_6$ alkyl groups, optionally substituted with at least one group chosen from hydroxyl, amino, halogen, such as chlorine, bromine and fluorine, and linear and branched $C_1$–$C_3$ alkoxy groups;
linear and branched $C_1$–$C_4$ alkoxy groups;
a group chosen from hydroxyl, amino, halogen and linear and branched $C_1$–$C_3$ alkoxy groups;
sulfonic groups;
Y is a divalent group, and
b) at least one synthetic dye different from the at least one dye of formula (I).

Also disclosed herein is a process for dyeing keratin fibers, such as human keratin fibers, for example, the hair, in which the above-mentioned dye composition is used, and also a multi-compartment device for implementing the process.

However, other characteristics and advantages of the present disclosure will emerge more clearly on reading the description that follows.

The compound of formula (I) included as ingredient in the dye composition according to the present disclosure will first be described.

As indicated above, this compound is represented by formula (I).

According to one embodiment, in this formula, the group Y is a $C_1$–$C_6$ alkylene group, optionally substituted at each end with a carbonyl group, or with a —CO—NH— or —NH—CO— group; a —CO—NH— or —NH—CO— group; a carbonyl group or an azo group.

In another embodiment, in formula (I), n is 1 and Y is a group —(CH$_2$)$_p$— with p being an integer ranging from 1 to 4.

In accordance with one embodiment, the compound of formula (I) corresponds to the following formula:

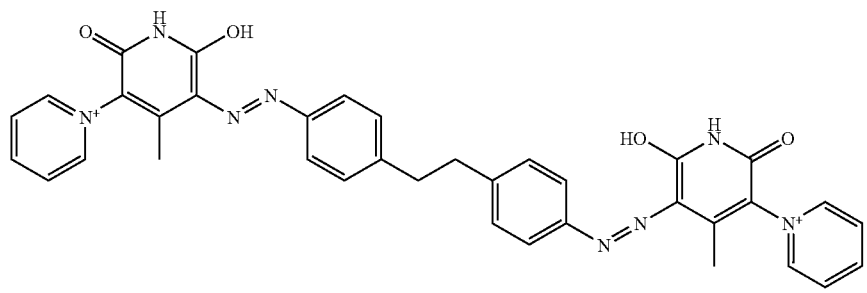

The dye composition according to the present disclosure comprises from 0.001% to 10% by weight of at least one compound of formula (I), such as from 0.005% to 5% by weight of the at least one compound of formula (I), relative to the total weight of the dye composition.

As mentioned above, the dye composition comprises, besides the at least one dye compound that has just been described, at least one synthetic dye different from the at least one dye of formula (I).

The term "different," as used herein, means a compound of a different family from that of the compounds of formula (I).

According to a first embodiment, the at least one synthetic dye is chosen from nonionic, cationic, anionic, amphoteric and zwitterionic direct dyes, and mixtures thereof.

Among the synthetic direct dyes that may be mentioned are, for example, acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bis-azine, bis-isoindoline, carboxanilide, coumarin, cyanin (for example azacarbocyanin, diazacarbocyanin, diazahemicyanin, hemicyanin and tetraazacarbocyanin), diazine, diketopyrrolopyrrole, dioxazine, diphenylamine, dithiazine, flavanthrone, flavone, fluorindine, formazan, hydrazone, hydroxy ketone, indamine, indanthrone, indigoid, indophenol, indoaniline, isoindoline, isoindolinone, isoviolanthrone, lactone, methine, naphthalimide, naphthanilide, naphtholactam, naphthoquinone, nitro, oxadiazole, oxazine, perilone, perinone, perylene, phenazine, phenothiazine, phthalocyanin, polyene/carotenoid, porphyrin, pyranthrone, pyrazolanthrone, pyrazolone, pyrimidinoanthrone, pyronine, quinacridone, quinoline, quinophthalone, squarane, stilbene, styryl, tetrazolium, thiazine, thioindigo, thiopyronine and xanthene dyes.

For example, at least one synthetic direct dye chosen from neutral, acidic and cationic nitrobenzene direct dyes, neutral, acidic and cationic azo direct dyes, neutral, acidic and cationic quinones, e.g., anthraquinone direct dyes, azine, triarylmethane and indoamine direct dyes, methines, styryls, porphyrins, metalloporphyrins, phthalocyanins, methine cyanins and fluorescent molecules may be used herein.

Among the nitro dyes that may be used, mention may be made in a non-limiting manner of the following dyes:
1,4-diamino-2-nitrobenzene
1-amino-2-nitro-4-(β-hydroxyethylamino)benzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene 1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino -4-nitrobenzene
1-β-hydroxyethylamino-4-β,γ-dihydroxypropyloxy -2-nitrobenzene
1-β,γ-dihydroxypropylamino-4-trifluoromethyl -2-nitrobenzene
1-β-hydroxyethylamino-4-trifluoromethyl -2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo dyes that may be used, non-limiting mention may be made of the cationic azo dyes described in patent applications WO 95/15144, WO 95/01772 and EP 714 954.

Among the azo dyes that may also be mentioned are those described in the Color Index International 3rd edition, such as: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Non-limiting mention may also be made of 1-(4'-aminodiphenylazo)-2-methyl-4-bis(β-hydroxyethyl)aminobenzene and 4-hydroxy-3-(2-methoxyph acid.

Among the quinone dyes that may be mentioned are, for example, the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes that may be mentioned are, for example, the following compounds: Basic Blue 17, and Basic Red 2.

Among the indoamine dyes that may be used, non-limiting mention may be made of the following compounds:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinoneimine;
3-N-(3'-chloro-4'-methylamino)phenylureido-6-methyl-1,4-benzoquinoneimine;
3-[4'-N-(ethylcarbamylmethyl)amino]phenylureido-6-methyl-1,4-benzoquinoneimine.

Non-limiting mention may also be made of the dyes described in documents U.S. Pat. No. 5,888,252, EP 1 133 975, WO 03/029359, EP 860 636, WO 95/01772 and EP 714954. Mention may also be made of those dyes mentioned in the encyclopaedia "The chemistry of synthetic dye" by K. Venkataraman, 1952, Academic Press, vol. 1 to 7, in encyclopaedia "Kirk-Othmer" "Chemical Technology", in the chapter "Dyes and Dye Intermediate", 1993, Wiley & Sons, and in various chapters of the encyclopaedia "Ullmann's Encyclopaedia of Industrial Chemistry" 7th edition, Wiley & Sons.

According to this embodiment, the at least one synthetic direct dye different from the at least one dye compound of formula (I) is present in an amount ranging from 0.001% to 10% relative to the total weight of the composition, for example from 0.005% to 5% relative to the total weight of the composition.

According to another embodiment of the invention, the at least one synthetic dye is chosen from at least one oxidation base optionally combined with at least one coupler.

Examples of oxidation bases that may be used include para-phenylenediamines, double bases, para-aminophenols, ortho-aminophenols and heterocyclic oxidation bases, alone or as a mixture, and also the acid-addition salts thereof.

Among the para-phenylenediamines that may be used, mention may be made, for example, of the compounds of formula (II) below, and the acid-addition salts thereof:

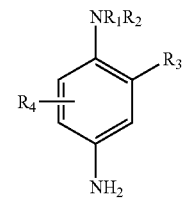

in which:
$R_1$ is chosen from a hydrogen atom, a $C_1$–$C_4$ alkyl radical, a $C_{11}$–$C_4$ monohydroxyalkyl radical, a $C_2$–$C_4$ polyhydroxyalkyl radical, a $(C_1$–$C_4)$alkoxy$(C_1$–$C_4)$alkyl radical, and a $C_1$–$C_4$ alkyl radical substituted with a nitrogenous group, a phenyl radical or a 4'-amino-phenyl radical;
$R_2$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical and a $C_1$–$C_4$ alkyl radical substituted with a nitrogenous group;
$R_3$ is chosen from a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino$(C_1$–$C_4)$alkoxy radical, a $C_1$–$C_4$ mesylaminoalkoxy radical and a carbamoylamino$(C_1$–$C_4)$alkoxy radical,
$R_4$ is chosen from a hydrogen atom, a halogen atom and a $C_1$–$C_4$ alkyl radical.

Among the para-phenylenediamines of formula (II) above, mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,β-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid-addition salts thereof.

As regards the double bases, these compounds comprise at least two aromatic nuclei bearing amino and/or hydroxyl groups linked together via a linker arm.

Among the double bases that may be used as oxidation bases in the dye compositions disclosed herein, non-limiting mention may be made of the compounds corresponding to formula (III) below, and the acid-addition salts thereof:

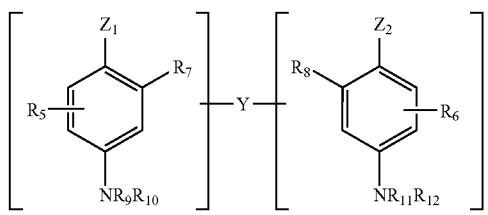

in which:

$Z_1$ and $Z_2$, which may be identical or different, are chosen from hydroxyl and —$NH_2$ radicals possibly substituted with a $C_1$–$C_4$ alkyl radical or with a linker arm Y;

the linker arm Y is a linear or branched alkylene chain comprising from 1 to 14 carbon atoms, and which may be interrupted by or terminated with at least one nitrogenous group and/or at least one hetero atom chosen from, for example, oxygen, sulfur and nitrogen atoms, and optionally substituted with at least one radical chosen from hydroxyl and $C_1$–$C_6$ alkoxy radicals;

$R_5$ and $R_6$ are chosen from, independently of each other, a hydrogen atom, a halogen atom, $C_1$–$C_4$ alkyl radicals, $C_1$–$C_4$ monohydroxyalkyl radicals, a $C_2$–$C_4$ polyhydroxyalkyl radicals, $C_1$–$C_4$ aminoalkyl radicals and a linker arm Y;

$R_7$, $R_8$, $R_9$, $R_{10}$, $R_{11}$ and $R_{12}$, which may be identical or different, are chosen from a hydrogen atom, a linker arm Y and $C_1$–$C_4$ alkyl radicals;

with the proviso that the compounds of formula (III) contain only one linker arm Y per molecule.

Among the nitrogenous groups of formula (III) above, non-limiting mention may be made, for example, of amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

Among the double bases of formula (III) above, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylene-diamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

Among the para-aminophenols that may be used as oxidation bases, mention may be made, for example, of the compounds corresponding to formula (IV) below, and the acid-addition salts thereof:

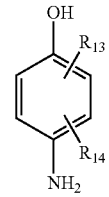

in which:

$R_{13}$ is chosen from a hydrogen atom, a halogen atom, and a radical chosen from $C_1$–$C_4$ alkyl, $C_1$–$C_4$ monohydroxyalkyl, ($C_1$–$C_4$)alkoxy($C_1$–$C_4$)alkyl, $C_1$–$C_4$ aminoalkyl and hydroxy($C_1$–$C_4$)alkylamino($C_1$–$C_4$)alkyl radicals, $R_{14}$ is chosen from a hydrogen atom, a halogen atom and a radical chosen from $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalk and ($C_1$–$C_4$)alkoxy-($C_1$–$C_4$)alkyl radicals, with the proviso that at least one of the radicals $R_{13}$ or $R_{14}$ is a hydrogen atom.

Para-aminophenols that may also be mentioned include 4-amino-6-[(5'-amino-2'-hydroxy-3'-methylphenyl)methyl]-2-methylphenol and bis(5-amino-2'-hydroxyphenyl)methane, and the acid-addition salts thereof.

Among the para-aminophenols of formula (IV) above, mention may be made, for example, of para-aminophenol, 4-amino-3-chlorophenol, 4-amino-2-chlorophenol, 2,6-dichloro-4-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid-addition salts thereof.

Among the ortho-aminophenols that may be used, mention may be made, for example, of 2-aminophenol, 2-amino-5-methylphenol, 2-amino-6-methylphenol and 5-acetamido-2-aminophenol, and the acid-addition salts thereof.

Among the heterocyclic bases that may be used as oxidation bases, mention may be made, for example, of pyridine derivatives, pyrimidine derivatives, pyrazole derivatives and pyrazolopyrimidine derivatives, and the acid-addition salts thereof.

Among the pyridine derivatives, mention may be made, for example, of the compounds described, for example, in patents GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid-addition salts thereof.

Among the pyrimidine derivatives, mention may be made, for example, of the compounds described, for example, in German patent DE 2 359 399 or Japanese patents JP 88-169 571 and JP 91-333 495 or patent application WO 96/15765, such as 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the acid-addition salts thereof.

Among the pyrazole derivatives, mention may be made, for example, of the compounds described in patents DE 3

843 892, DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-d 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid-addition salts thereof.

Among the pyrazolopyrimidine derivatives, mention may be made more, for example, of the pyrazolo[1,5-a]pyrimidines of formula (V) below, and the addition salts thereof with an acid or with a base and the tautomeric forms thereof, when a tautomeric equilibrium exists:

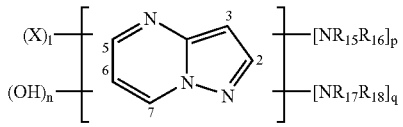

in which:

$R_{15}$, $R_{16}$, $R_{17}$ and $R_{18}$, which may be identical or different, are chosen from a hydrogen atom, $C_1$–$C_4$ alkyl radicals, aryl radicals, $C_1$–$C_4$ hydroxyalkyl radicals, $C_2$–$C_4$ polyhydroxyalkyl radicals, ($C_1$–$C_4$)alkoxy($C_1$–$C_4$)alkyl radicals, $C_1$–$C_4$ aminoalkyl radicals, wherein the amine may be protected with an acetyl, ureido or sulfonyl radical, ($C_1$–$C_4$)alkylamino($C_1$–$C_4$)alkyl radicals, di[($C_1$–$C_4$)alkyl]amino($C_1$–$C_4$)alkyl radicals, wherein the dialkyl radicals may form a 5- or 6-membered carbon-based ring or a heterocycle, hydroxy($C_1$–$C_4$)alkyl-amino($C_1$–$C_4$) alkyl radicals, and di[hydroxy($C_1$–$C_4$)alkyl]-amino ($C_1$–$C_4$)alkyl radicals;

the radicals X, which may be identical or different, are chosen from a hydrogen atom, $C_1$–$C_4$ alkyl radicals, aryl radicals, $C_1$–$C_4$ hydroxyalkyl radicals, $C_2$–$C_4$ polyhydroxyalkyl radicals, $C_1$–$C_4$ aminoalkyl radicals, ($C_1$–$C_4$) alkylamino($C_1$–$C_4$)alkyl radicals, di[($C_1$–$C_4$)alkyl]amino ($C_1$–$C_4$)alkyl radicals, wherein the dialkyls may form a 5- or 6-membered carbon-based ring or a heterocycle, hydroxy($C_1$–$C_4$)alkyl-amino($C_1$–$C_4$)alkyl radicals, di-[hydroxy($C_1$–$C_4$)alkyl]amino($C_1$ radicals, amino radicals, ($C_1$–$C_4$)alkyl-amino radicals, di[($C_1$–$C_4$)alkyl]-amino radicals; a halogen atom, a carboxylic acid group, and a sulfonic acid group;

i is equal to 0, 1, 2 or 3; p is equal to 0 or 1; q is equal to 0 or 1; n is equal to 0 or 1the proviso that the sum p+q is other than 0;

when p+q is equal to 2, then n is equal to 0 and the groups $NR_{15}R_{16}$ and $NR_{17}R_{18}$ occupy the (2,3); (5,6); (6,7); (3,5) or (3,7) positions;

when p+q is equal to 1, then n is equal to 1 and the group $NR_{15}R_{16}$ (or $NR_{17}R_{18}$) and the OH group occupy the (2,3); (5,6); (6,7); (3,5) or (3,7) positions.

Among the pyrazolo[1,5-a]pyrimidines of formula (V) above, mention may be made, for example, of pyrazolo-[1,5-a]pyrimidine-3,7-diamine; 2,5-dimethylpyrazolo[1,5-a] pyrimidine-3,7pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7yl)-(2hydroxyethyl)amino]ethanol; 2-[(7-aminopyrazolo [1,5-a]pyrimidin-3-yl)(2-hydroxy-ethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; and the addition salts thereof and the tautomeric forms thereof, when a tautomeric equilibrium exists.

When the dye composition comprises one or more oxidation bases, they may be present in an amount ranging from 0.0005% to 12% by weight, such as from 0.005% to 8% by weight relative to the total weight of the dye composition.

The dye composition may also comprise at least one coupler combined with the at least one oxidation base.

These couplers are chosen, for example, from those conventionally used in oxidation dye compositions, i.e., meta-phenylenediamines, meta-aminophenols, meta-diphenols and heterocyclic couplers, and the acid-addition salts thereof.

These couplers may be chosen, for example, from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the acid-addition salts thereof.

When present in the dye composition, the at least one coupler may be present in an amount ranging from 0.0001% to 10% by weight, such as from 0.005% to 5% by weight relative to the weight of the dye composition.

In general, the acid-addition salts that may be used in the context of the dye compositions of the invention may be chosen from the hydrochlorides, hydrobromides, sulfates, tartrates, lactates and acetates.

The composition disclosed herein may also comprise various conventionally used adjuvants, such as anionic, cationic, nonionic, amphoteric or zwitterionic surfactants, or mixtures thereof, anionic, cationic, nonionic, amphoteric or zwitterionic polymers, mineral thickeners, associative or non-associative thickening polymers, antioxidants, sequestering agents, penetrating agents, fragrances, buffers, dispersants, conditioning agents, for instance cations, volatile or non-volatile, modified or unmodified silicones, cationic amphiphilic polymers, film-forming agents, ceramides, vitamins or provitamins, preserving agents, stabilizers, opacifiers or matting agents, for instance titanium dioxide, mineral fillers, for instance clays, silicas, especially fumed silicas of hydrophilic or hydrophobic nature, binding polymers such as vinylpyrrolidone, sunscreens.

The adjuvants mentioned above are generally present in an amount for each of them ranging from 0.01% to 20% by weight relative to the weight of the dye composition.

The medium of the dye composition is a cosmetically acceptable medium. It advantageously comprises water or a mixture of water and of at least one organic solvent.

Examples of organic solvents that may be mentioned include linear or branched, in one embodiment saturated, monoalcohols comprising from 2 to 10 carbon atoms, such as ethyl alcohol or isopropyl alcohol; aromatic alcohols such as benzyl alcohol or phenylethyl alcohol; polyols or polyol ethers, for instance ethylene glycol monomethyl ether, monoethyl ether and monobutyl ether, propylene glycol or ethers thereof, for instance propylene glycol monomethyl ether, butylene glycol, dipropylene glycol, hexylene glycol (2-methyl-2,4-pentanediol), neopentyl glycol and 3-methyl-1,5-pentanediol; and also diethylene glycol alkyl ethers, for instance, of $C_1$–$C_4$, for instance diethylene glycol monoethyl ether or monobutyl ether, alone or as a mixture.

When present, the at least one organic solvent described above may be present in an amount ranging from 1% to 40% by weight and for example, from 5% to 30% by weight relative to the total weight of the dye composition.

It should be noted that the composition according to the invention may be in various galenical forms, such as a lotion, a cream or a gel, or in any other form that is suitable for dyeing keratin fibers. It may also be packaged under pressure in an aerosol can in the presence of a propellant, and form a mousse.

The dye composition used herein may also optionally comprise at least one oxidizing agent.

The at least one oxidizing agent may be chosen from hydrogen peroxide, alkali metal or alkaline-earth metal peroxides, for instance sodium, potassium or magnesium peroxide; urea peroxide, alkali metal bromates or ferricyanides, persalts such as alkali metal or alkaline-earth metal perborates and persulfates, for instance those of sodium, potassium or magnesium, alone or as mixtures. The at least one oxidizing agent may also be chosen from enzymes such as peroxidases and two-electron or four-electron oxidoreductases. In one embodiment, the at least one oxidizing agent is hydrogen peroxide.

When it is present, the at least one oxidizing agent is present in an amount ranging from 0.001% to 20% by weight relative to the total weight of the dye composition.

If the composition used in the process disclosed herein comprises an oxidizing agent, then this composition, also referred to as a ready-to-use composition, results from the mixing of the composition described previously, free of oxidizing agent, with a composition comprising at least one such agent (this composition is then referred to as an oxidizing composition). In this case, the mixture is prepared before applying the ready-to-use composition to the fibers to be treated.

The medium of the above-mentioned oxidizing composition is, for example, water or a mixture of water and of organic solvent.

Finally, the oxidizing composition may comprise additives that are common in the field, for instance surfactants, thickeners, antioxidants, fragrances, dispersants, conditioning agents, sequestering agents, preserving agents.

It should be pointed out that the lists of solvents and additives, and the contents thereof, indicated in the context of the description of the dye composition remain valid and reference may be made thereto.

The pH of the dye composition used in the process disclosed herein ranges from 3 to 12, such as from 5 to 11 and, for example, from 6 to 8.5.

It may be adjusted to the desired value using acidifying or basifying agents.

Among the acidifying agents that may be mentioned as examples are mineral or organic acids, for instance hydrochloric acid, orthophosphoric acid, sulfuric acid or acetic acid.

Among the basifying agents that may be mentioned as examples are aqueous ammonia, alkaline carbonates, alkanolamines such as monoethanolamine, diethanolamine and triethanolamine and also derivatives thereof, sodium hydroxide, potassium hydroxide and the compounds of formula (A) below:

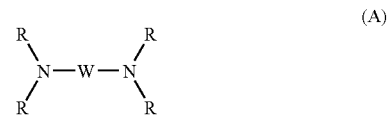

(A)

in which W is a propylene residue optionally substituted with a hydroxyl group or a $C_1$–$C_6$ alkyl radical; the radicals R, which may be identical or different, represent a hydrogen atom or a $C_1$–$C_6$ alkyl or $C_1$–$C_6$ hydroxyalkyl radical.

Also disclosed herein is a process for dyeing keratin fibers, such as human keratin fibers, in which the wet or dry keratin fibers are placed in contact with a dye composition according to the invention, for a time that is sufficient to develop the desired coloration.

More particularly, the process comprises:
a) placing the wet or dry fibers in contact with the composition that has just been described, for a time that is sufficient to develop the coloration,
b) optionally rinsing the fibers,
c) optionally washing and rinsing the fibers,
d) drying the fibers or leaving them to dry.

According to one embodiment, the composition applied to the fibers does not comprise an oxidizing agent.

This embodiment is relevant when the composition comprises only the compound(s) of formula (I) and at least one synthetic dye chosen from direct dyes. In this embodiment, it may be envisaged not to rinse or wash the fibers with shampoo once they have been treated.

According to another embodiment, the composition applied to the fibers comprises at least one oxidizing agent. This embodiment applies to any type of dye composition, whether or not this composition comprises, among synthetic dyes, at least one oxidation base optionally combined with at least one coupler.

According to this embodiment, the composition intended to be applied to the fibers, i.e. the ready-to-use composition, is prepared extemporaneously before the application, by mixing at least one dye composition, free of oxidizing agent, at least one of which comprises at least one compound of formula (I), and at least one other comprises at least one synthetic dye different from the compound of formula (I) (these two compositions possibly being the same), with a composition comprising at least one oxidizing agent.

Thus, it may be envisaged, for example, to start with a dye composition comprising both the compound of formula (I) and the synthetic dye different from the compound of formula (I), or alternatively to start with two or more dye compositions, at least one comprising the compound of formula (I) and at least one other comprising the synthetic dye(s) different from the compound of formula (I).

The pH of the oxidizing composition containing the oxidizing agent is such that, after mixing with the dye composition, the pH of the resulting composition applied to the keratin fibers ranges from 3 to 12, such as from 5 to 11. It may be adjusted to the desired value by means of acidifying agents, basifying agents or buffers usually used in the dyeing of keratin fibers and as defined above.

According to this possibility, one may separately store, on the one hand, the dye composition(s) free of oxidizing agent, and, on the other hand, an oxidizing composition.

Still according to this embodiment of the process, it may be envisaged to successively apply, in either order, the dye composition(s) and the composition comprising at least one oxidizing agent, with or without intermediate rinsing, or alternatively to apply these two compositions simultaneously.

The time required to develop the coloration may range from 1 to 60 minutes, such as from 5 to 45 minutes, for example from 10 to 20 minutes.

Moreover, conventionally, step a) of the process may be performed at a temperature ranging from room temperature (about 15 to 25° C.) and 80° C., for instance at a temperature ranging from 25 to 55° C.

Once step a) is complete, the fibers may optionally be rinsed (step b) and optionally washed with a shampoo and then rinsed (step c). For example, the fibers may be rinsed and washed with a shampoo.

Finally, the fibers are dried or are left to dry, for example at a temperature from 20 to 220° C.

Finally, also disclosed herein is a multi-compartment device for implementing the process that has just been described and that uses an oxidizing composition. This device comprises a compartment comprising a dye composition comprising at least one compound of formula (I) and optionally at least one synthetic dye different from the compound of formula (I); optionally at least one second compartment comprising a dye composition comprising at least one synthetic dye different from the compound of formula (I), and at least one third compartment comprising a composition comprising at least one oxidizing agent.

What is claimed is:

1. A dye composition comprising, in a medium that is suitable for dyeing keratin fibers:

a) at least one dye of formula (I) below:

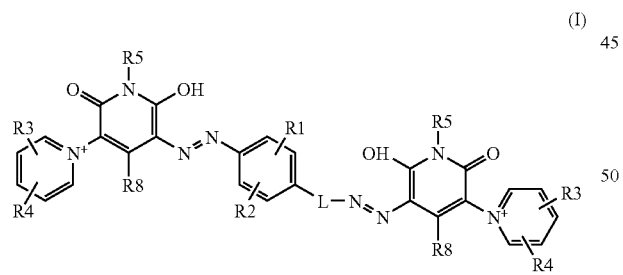

(I)

in which:

$R_1$ and $R_2$ are chosen from, independently of each other:
 a hydrogen atom;
 linear and branched $C_1$–$C_4$ alkyl groups, optionally substituted with at least one group chosen from hydroxyl, amino, halogen, and $C_1$–$C_3$ alkyl groups;
 linear and branched $C_1$–$C_4$ alkoxy groups;
 a group chosen from hydroxyl, amino, halogen, and linear and branched $C_1$–$C_3$ alkoxy groups;

$R_3$ and $R_4$ are chosen from, independently of each other:
 a hydrogen atom;
 linear and branched $C_1$–$C_4$ alkyl groups;
 a group chosen from carboxylic groups, in acid or salified form, and linear and branched, $C_1$–$C_6$ carboxyalkyl groups;
 linear and branched $C_1$–$C_6$ alkoxy groups;

$R_5$ is chosen from:
 a hydrogen atom;
 a linear or branched $C_1$–$C_4$ alkyl group;
 a linear or branched $C_1$–$C_6$ alkenyl group, substituted with a group $(R_6R_7N)_n$, n being equal to 0 or 1 and, when n=1, $R_6$ and $R_7$ are, independently of each other, chosen from a hydrogen atom and linear and branched $C_1$–$C_6$ alkyl groups, optionally substituted with at least one group chosen from hydroxyl, amino, halogen, and $C_1$–$C_3$ alkyl groups;

$R_8$ is chosen from:
 a hydrogen atom;
 a linear or branched $C_1$–$C_6$ alkyl group;

L is a divalent group of formula L1 or L2 below:

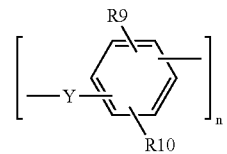

L1

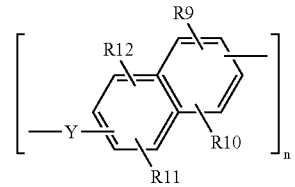

L2 in which:

n is equal to 0 or 1;

$R_9$, $R_{10}$, $R_{11}$ or $R_{12}$ are chosen from, independently of each other:
 a hydrogen atom;
 linear and branched $C_1$–$C_6$ alkyl groups, optionally substituted with at least one group chosen from hydroxyl, amino, halogen, and linear and branched $C_1$–$C_3$ alkoxy groups;
 linear or branched $C_1$–$C_4$ alkoxy groups;
 a group chosen from hydroxyl, amino, halogen and linear and branched $C_1$–$C_3$ alkoxy groups;
 sulfonic groups;

Y is a divalent group, and b) at least one synthetic dye different from the at least one dye of formula (I).

2. A dye composition according to claim 1, wherein, in formula (I), the group Y is an alkylene group of 1 to 4 carbon atoms, optionally substituted at each end with a carbonyl group, or with a —CO—NH— or —NH—CO— group; a —CO—NH— or —NH—CO— group; a carbonyl group or an azo group.

3. A dye composition according to claim 2, wherein n is 1 and Y is —(CH$_2$)$_p$— with p being an integer from 1 to 4.

4. A dye composition according to claim 1, wherein the compound of formula (I) corresponds to a compound of the following formula:

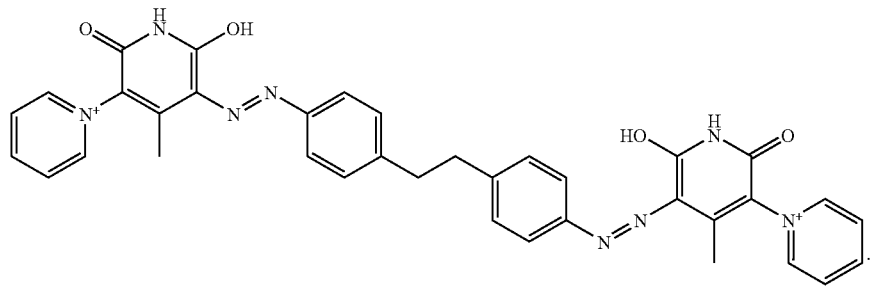

5. A dye composition according to claim 1, wherein the at least one dye compound of formula (I) is present in an amount ranging from 0.01% to 10% by weight relative to the total weight of the dye composition.

6. A dye composition according to claim 1, wherein the at least one synthetic dye different from the compound of formula (I) is chosen from nonionic, cationic, anionic, amphoteric and zwitterionic direct dyes.

7. A dye composition according to claim 6, wherein the at least one synthetic direct dye is chosen from acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bis-azine, bis-isoindoline, carboxanilide, coumarin, cyanin, diazine, diketopyrrolopyrrole, dioxazine, diphenylamine, dithiazine, flavanthrone, flavone, fluorindine, formazan, hydrazone, hydroxy ketone, indamine, indanthrone, indigoid, indophenol, indoaniline, isoindoline, isoindolinone, isoviolanthrone, lactone, methine, naphthalimide, naphthanilide, naphtholactam, naphthoquinone, nitro, oxadiazole, oxazine, perilone, perinone, perylene, phenazine, phenothiazine, phthalocyanin, polyene/carotenoid, porphyrin, pyranthrone, pyrazolanthrone, pyrazolone, pyrimidinoanthrone, pyronine, quinacridone, quinoline, quinophthalone, squarane, stilbene, styryl, tetrazolium, thiazine, thioindigo, thiopyronine and xanthene dyes.

8. A dye composition according to claim 6, wherein the at least one synthetic direct dye is chosen from neutral, acidic and cationic nitrobenzene direct dyes, neutral, acidic and cationic azo direct dyes, neutral, acidic and cationic quinone, azine, triarylmethane and indoamine direct dyes, methines, styryls, porphyrins, metalloporphyrins, phthalocyanins, methine cyanins, and fluorescent molecules.

9. A dye composition according to claim 1, wherein the at least one synthetic direct dye, different from the compound of formula (I), is present in an amount ranging from 0.001% to 10% by weight relative to the total weight of the dye composition.

10. A dye composition according to claim 1, wherein the at least one synthetic dye is chosen from at least one oxidation base optionally combined with at least one coupler.

11. A dye composition according to claim 10, wherein the at least one oxidation base is chosen from para-phenylenediamines, double bases, para-aminophenols, ortho-aminophenols and heterocyclic oxidation bases, and the acid-addition salts thereof.

12. A dye composition according to claim 10, wherein the at least one oxidation base is present in an amount ranging from 0.0005% to 12% by weight relative to the total weight of the dye composition.

13. A dye composition according to claim 10, wherein the at least one coupler is chosen from meta-phenylenediamines, meta-aminophenols, meta-diphenols and heterocyclic couplers, and the acid-addition salts thereof.

14. A dye composition according to claim 1, wherein the composition further comprising at least one oxidizing agent.

15. A dye composition according to claim 14, wherein the at least one oxidizing agent is chosen from hydrogen peroxide, urea peroxide, alkali metal bromates and ferricyanides, persalts, redox enzymes, peroxidases and two-electron oxidoreductases, where appropriate in the presence of the respective donor thereof.

16. A process for dyeing keratin fibers, comprising
placing wet or dry keratin fibers in contact with a dye composition for a time sufficient to develop a desired coloration, the dye composition comprising, in a medium suitable for dyeing keratin fibers
a) at least one dye of formula (I) below:

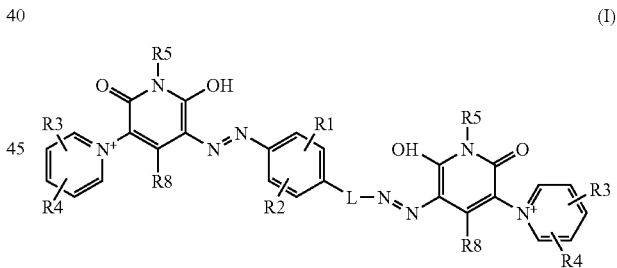

(I)

in which:
$R_1$ and $R_2$ are chosen from, independently of each other:
a hydrogen atom;
linear and branched $C_1$–$C_4$ alkyl groups, optionally substituted with at least one group chosen from hydroxyl, amino, halogen, and $C_1$–$C_3$ alkyl groups;
linear and branched $C_1$–$C_4$ alkoxy groups;
a group chosen from hydroxyl, amino, halogen and linear and branched $C_1$–$C_3$ alkoxy groups;
$R_3$ and $R_4$ are chosen from, independently of each other:
a hydrogen atom;
linear and branched $C_1$–$C_4$ alkyl groups;
a group chosen from carboxylic groups, in acid or salified form, and linear and branched, $C_1$–$C_6$ carboxyalkyl groups;
linear and branched $C_1$–$C_6$ alkoxy groups;

$R_5$ is chosen from:
- a hydrogen atom;
- a linear or branched $C_1$–$C_4$ alkyl group;
- a linear or branched $C_1$–$C_6$ alkenyl group, substituted with a group $(R_6R_7N)_n$, n being equal to 0 or 1 and, when n=1, $R_6$ and $R_7$ are, independently of each other, chosen from a hydrogen atom and linear and branched $C_1$–$C_6$ alkyl groups, optionally substituted with at least one group chosen from hydroxyl, amino, halogen, and $C_1$–$C_3$ alkyl groups;

$R_8$ is chosen from:
- a hydrogen atom;
- a linear or branched $C_1$–$C_6$ alkyl group;

L is a divalent group of formula L1 or L2 below:

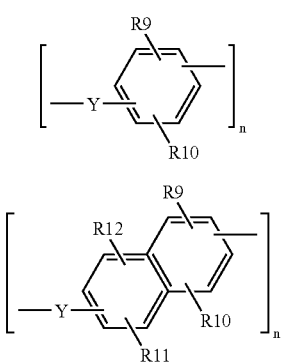

in which:
- n is equal to 0 or 1;
- $R_9$, $R_{10}$, $R_{11}$ or $R_{12}$ are chosen from, independently of each other:
  - a hydrogen atom;
  - linear and branched $C_1$–$C_6$ alkyl groups, optionally substituted with at least one group chosen from hydroxyl, amino, halogen, and linear and branched $C_1$–$C_3$ alkoxy groups;
  - linear and branched $C_1$–$C_4$ alkoxy groups;
  - a group chosen from hydroxyl, amino, halogen and linear and branched $C_1$–$C_3$ alkoxy groups;
  - sulfonic groups;

Y is a divalent group, and b) at least one synthetic dye different from the at least one dye of formula (I).

17. A dyeing process according to claim 16, wherein the composition is prepared extemporaneously before application, by mixing a composition comprising at least one compound of formula (I) and at least one synthetic dye different from the compound of formula (I), with a composition comprising at least one oxidizing agent.

18. A dyeing process according to claim 17, wherein the composition is prepared extemporaneously before application, by mixing a composition comprising at least one compound of formula (I) and a composition comprising at least one synthetic dye different from the compound of formula (I), with a composition comprising at least one oxidizing agent.

19. A process according to claim 16, wherein the at least one dye composition and the composition comprising at least one oxidizing agent are applied successively in either order.

20. A multi-compartment device for dyeing keratin fibers, comprising
- at least one first compartment comprising a dye composition comprising at least one compound of formula (I) according to claim 1, and optionally at least one synthetic dye different from the compound of formula (I);
- at least one second compartment comprising a composition comprising at least one oxidizing agent, and
- optionally at least one third compartment comprising a dye composition comprising at least one synthetic dye different from the compound of formula (I).

* * * * *

UNITED STATES PATENT AND TRADEMARK OFFICE
CERTIFICATE OF CORRECTION

PATENT NO. : 7,217,299 B2  Page 1 of 1
APPLICATION NO. : 11/030053
DATED : May 15, 2007
INVENTOR(S) : Sylvain Kravtchenko et al.

It is certified that error appears in the above-identified patent and that said Letters Patent is hereby corrected as shown below:

Title Page, item (54), line 5 of Title, "DYE, AND PROCESS" should read --DYE, AND PROCESS FOR DYEING KERATIN FIBERS--.

Claim 6, col. 15, line 24, "zwifterionic" should read --zwitterionic--

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,217,299 B2  
APPLICATION NO. : 11/030053  
DATED : May 15, 2007  
INVENTOR(S) : Sylvain Kravtchenko et al.

Page 1 of 1

It is certified that error appears in the above-identified patent and that said Letters Patent is hereby corrected as shown below:

Title Page, item (54) and Column 1, line 5 of Title, "DYE, AND PROCESS" should read --DYE, AND PROCESS FOR DYEING KERATIN FIBERS--.

Claim 6, col. 15, line 24, "zwifterionic" should read --zwitterionic--

This certificate supersedes the Certificate of Correction issued June 10, 2008.

Signed and Sealed this

Fifteenth Day of July, 2008

JON W. DUDAS  
*Director of the United States Patent and Trademark Office*